US012642710B2

(12) United States Patent
Manabe

(10) Patent No.: US 12,642,710 B2
(45) Date of Patent: Jun. 2, 2026

(54) COMPOSITE STRETCHABLE MEMBER AND WEARABLE ARTICLE USING SAME

(71) Applicant: ZUIKO CORPORATION, Osaka (JP)

(72) Inventor: Takahito Manabe, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 1119 days.

(21) Appl. No.: 17/612,084

(22) PCT Filed: May 15, 2020

(86) PCT No.: PCT/JP2020/019486
§ 371 (c)(1),
(2) Date: Nov. 17, 2021

(87) PCT Pub. No.: WO2020/235495
PCT Pub. Date: Nov. 26, 2020

(65) Prior Publication Data
US 2022/0211553 A1      Jul. 7, 2022

(30) Foreign Application Priority Data

May 22, 2019    (JP) ................................. 2019-096159

(51) Int. Cl.
*A61F 13/49*          (2006.01)
*A61F 13/15*          (2006.01)
(52) U.S. Cl.
CPC ................... *A61F 13/49011* (2013.01); *A61F 2013/15869* (2013.01); *A61F 2013/49025* (2013.01)
(58) Field of Classification Search
CPC ...... A61F 13/49011; A61F 2013/15869; A61F 2013/49025; A61F 13/4902; A61F 13/49012
See application file for complete search history.

(56) References Cited

U.S. PATENT DOCUMENTS 11,607,351 B2 *    3/2023   Zink ......................... B32B 5/26
2003/0031834 A1    2/2003   Ukegawa et al.
(Continued)

FOREIGN PATENT DOCUMENTS

CN            1849187        10/2006
CN          101896336        11/2010
(Continued)

OTHER PUBLICATIONS

Extended European Search Report issued May 24, 2022 in corresponding European Patent Application No. 20809054.8.
(Continued)

*Primary Examiner* — Rebecca E Eisenberg
*Assistant Examiner* — Gabriella E Burnette
(74) *Attorney, Agent, or Firm* — Wenderoth, Lind & Ponack, L.L.P.

(57)          ABSTRACT

Provided are a composite stretchable member and wearing article capable of improving design properties at the time of contraction. A composite stretchable member stretchable in a specific direction includes two sheets facing each other, and a plurality of elastic members extending along the specific direction and being stretchable in the specific direction between the sheets. The sheets are bonded to each other at first bonding sections. Each first bonding section continuously extends along the intersecting direction intersecting the specific direction and intersects the elastic members. Each elastic member is bonded to each sheet at an intersection with the corresponding one of the first bonding sections. Each first bonding section has a wavy-line-shape extending in the intersecting direction with convex portions and concave portions that alternately appear continuously. Two adjacent first bonding sections are disposed with the convex portions or the concave portions that at least partially overlap each other.

13 Claims, 14 Drawing Sheets

(56) References Cited

U.S. PATENT DOCUMENTS

| | | | |
|---|---|---|---|
| 2005/0095942 | A1 | 5/2005 | Mueller et al. |
| 2011/0308688 | A1 | 12/2011 | Bestgen et al. |
| 2015/0126956 | A1 | 5/2015 | Raycheck et al. |
| 2018/0140473 | A1 | 5/2018 | Koshijima et al. |
| 2019/0021916 | A1 | 1/2019 | Ishikawa |
| 2020/0155370 | A1 | 5/2020 | Ohtsubo |

FOREIGN PATENT DOCUMENTS

| | | | |
|---|---|---|---|
| EP | 3296100 | A1 * | 3/2018 ....... A61F 13/15593 |
| JP | 2019-97926 | | 6/2019 |
| JP | 2019-97927 | | 6/2019 |
| WO | 2016/208513 | | 12/2016 |
| WO | 2019/069807 | | 4/2019 |

OTHER PUBLICATIONS

International Search Report issued Jul. 14, 2020 in International (PCT) Application No. PCT/JP2020/019486.

First Office Action issued Mar. 28, 2024 in corresponding Chinese Patent Application No. 2020800371363, with English language translation.

\* cited by examiner

COMPOSITE STRETCHABLE MEMBER AND WEARABLE ARTICLE USING SAME

TECHNICAL FIELD

The present invention relates to a composite stretchable member stretchable in a specific direction and a wearing article using the same.

BACKGROUND ART

Wearing articles such as a disposable diaper having a waistline portion and a crotch portion have been known. In these wearing articles, the waistline portion of the wearing article may be formed of a composite stretchable member, which is stretchable, to improve wearing comfort.

As the composite stretchable member, for example, a member described in Patent Literature 1 is known.

The member described in Patent Literature 1 includes two sheets and a plurality of elastic members. These two sheets are bonded by a linear heat fusion line extending in a direction intersecting an extending direction of each elastic member. As a result, the sheets, or the sheets and the elastic members, are intermittently bonded to each other.

When a wearing article having a waistline portion as described above is manufactured, it is desired to improve design properties of the wearing article by giving various changes in shape to pleats generated when a waistline member contracts. However, a composite stretchable member as described above merely has a monotonous pattern when the composite stretchable member contracts, the monotonous pattern being formed by pleats that are each linearly formed along the heat fusion line, and thus improvement in design properties is difficult.

CITATION LIST

Patent Literature

Patent Literature 1: International Publication WO 2016/ 208513 A

SUMMARY OF INVENTION

It is an object of the present invention to provide a composite stretchable member capable of improving design properties at the time of contraction, and a wearing article using the same.

To solve the problem, a composite stretchable member of the present invention is stretchable in a specific direction and includes two sheets facing each other, and a plurality of elastic members extending along the specific direction and being stretchable in the specific direction between the sheets, the sheets being bonded to each other at a plurality of first bonding sections, each of the first bonding sections continuously extending along an intersecting direction intersecting the specific direction to intersect the plurality of elastic members, each of the elastic members being bonded to each of the sheets at an intersection with the corresponding one of the first bonding sections, each of the first bonding sections having a wavy line shape extending in the intersecting direction with convex portions and concave portions that alternately appear continuously, and being disposed in a state where the convex portions and the concave portions are overlapped each other when viewed from the specific direction in at least a part of two adjacent first bonding sections.

BRIEF DESCRIPTION OF DRAWINGS

FIG. 4 is a view corresponding to FIG. 1 and schematically illustrating a bonding section.

FIG. 12 is a sectional view taken along line XII-XII in FIG. 11.

DESCRIPTION OF EMBODIMENTS

Hereinafter, embodiments of the present invention will be described with reference to the accompanying drawings. The following embodiments are merely examples embodying the present invention, and do not limit the technical scope of the present invention.

(1) Configuration of Composite Stretchable Member

Figure 1:
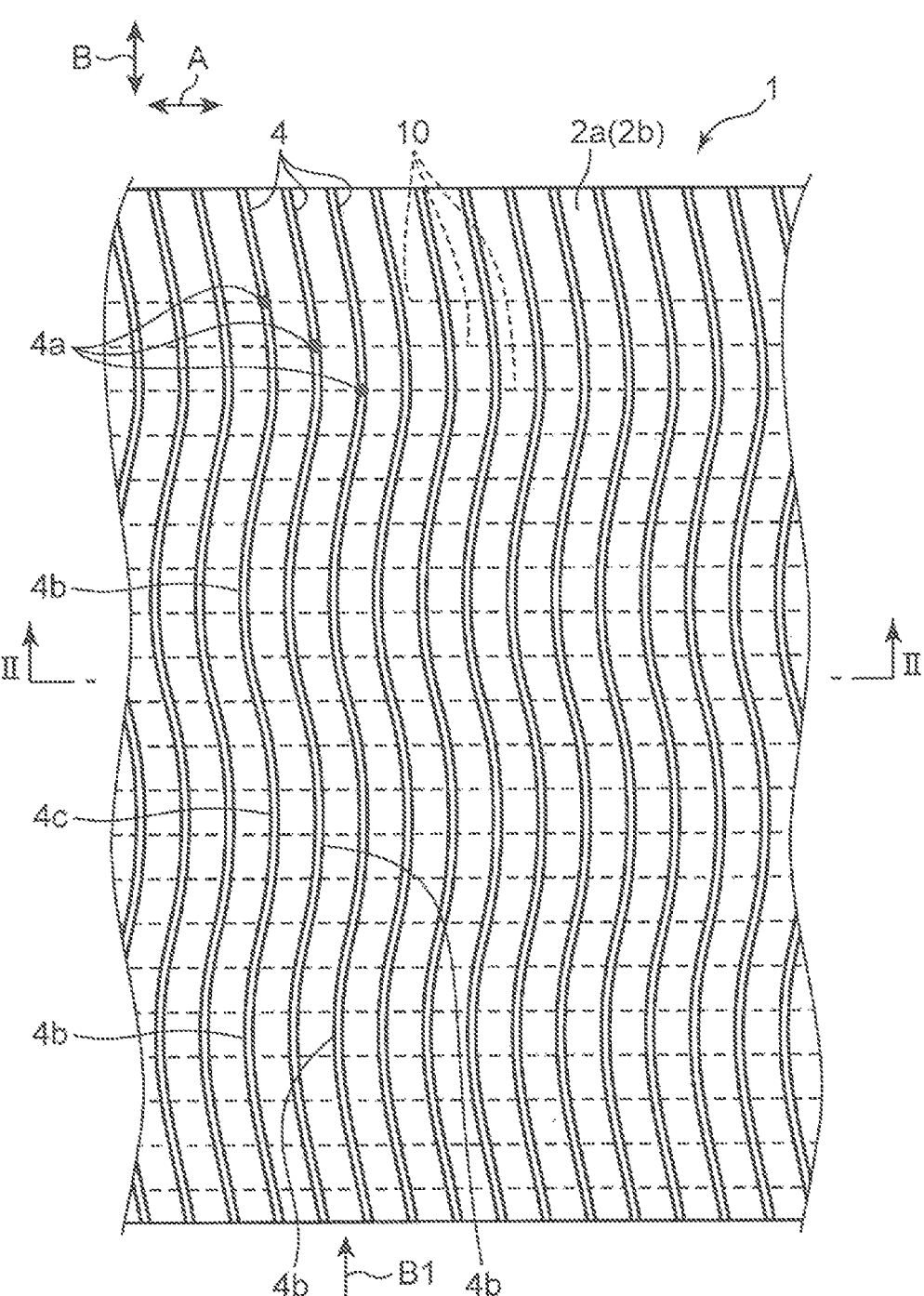
FIG. 1 is a plan view of a composite stretchable member according to an embodiment of the present invention.
Figure 2:
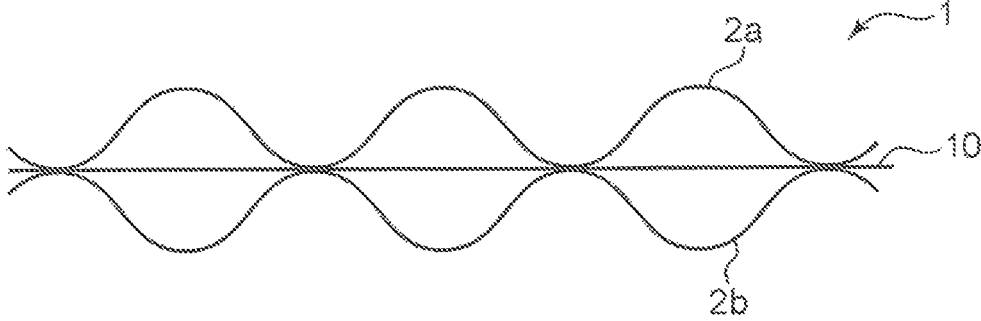
FIG. 2 is a part of a sectional view taken along line II-II in FIG. 1.

FIG. 1 is a plan view of a composite stretchable member according to an embodiment of the present invention. FIG. 2 is a part of a sectional view taken along line II-II in FIG. 1.

A composite stretchable member 1 includes two elongated sheets 2a, 2b facing each other, and a plurality of elongated elastic members 10 stretchable in a longitudinal direction A that is a specific direction. Each of the elastic members 10 is disposed between the sheets 2a, 2b so as to be stretchable in the longitudinal direction A (the left-right direction in FIG. 1) of each of the sheets 2a, 2b, so as to extend and contract in the longitudinal direction A of each of the sheets 2a, 2b along the longitudinal direction A. In the present embodiment, the elastic members 10 are disposed at equal intervals in a width direction B (an intersecting direction orthogonal to the longitudinal direction A of the sheets 2a, 2b) of the sheets 2a, 2b, and extend parallel to the longitudinal direction A of the sheets 2a, 2b.

In the present embodiment, a sheet-like material such as a nonwoven fabric is used as the sheets 2a, 2b.

An elastic member 10 is made of a material that is more elastic than the material (nonwoven fabric or the like) of the sheets 2a, 2b. In the present invention, the material of the elastic member 10 is not particularly limited.

Figure 3:
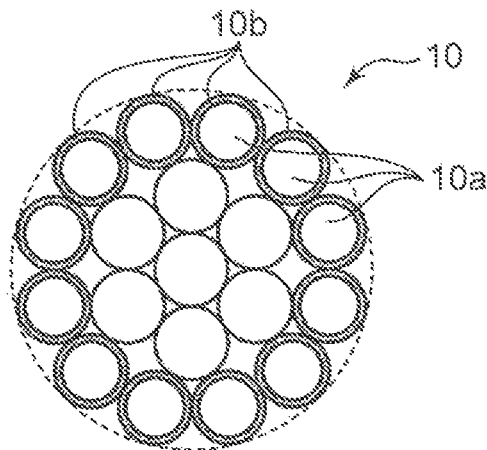
FIG. 3 is a schematic sectional view illustrating a section of an elastic member.

As an example of the present embodiment is illustrated in FIG. 3, the elastic member 10 is a multi-strand provided with a plurality of rubber threads (fibrous elastic bodies) 10*a* collected in a bundle, and includes at least some of the rubber threads 10*a* each having the periphery covered with a covering layer 10*b*, for example. Specifically, the rubber threads 10*a* disposed particularly in an outer peripheral portion among the plurality of rubber threads 10*a* are each covered with the covering layer 10*b*. Every rubber thread 10*a* may be covered with the covering layer 10*b*.

As the material of the rubber thread 10*a*, for example, polyurethane is used. As the material of the covering layer 10*b*, for example, a lubricant such as silicon oil or magnesium stearate is used.

FIG. 1 illustrates a plurality of first bonding sections 4 in a wavy line shape on which the sheets 2*a*, 2*b* are bonded to each other, and the sheets 2*a*, 2*b* are bonded to the elastic members 10.

Figure 4:
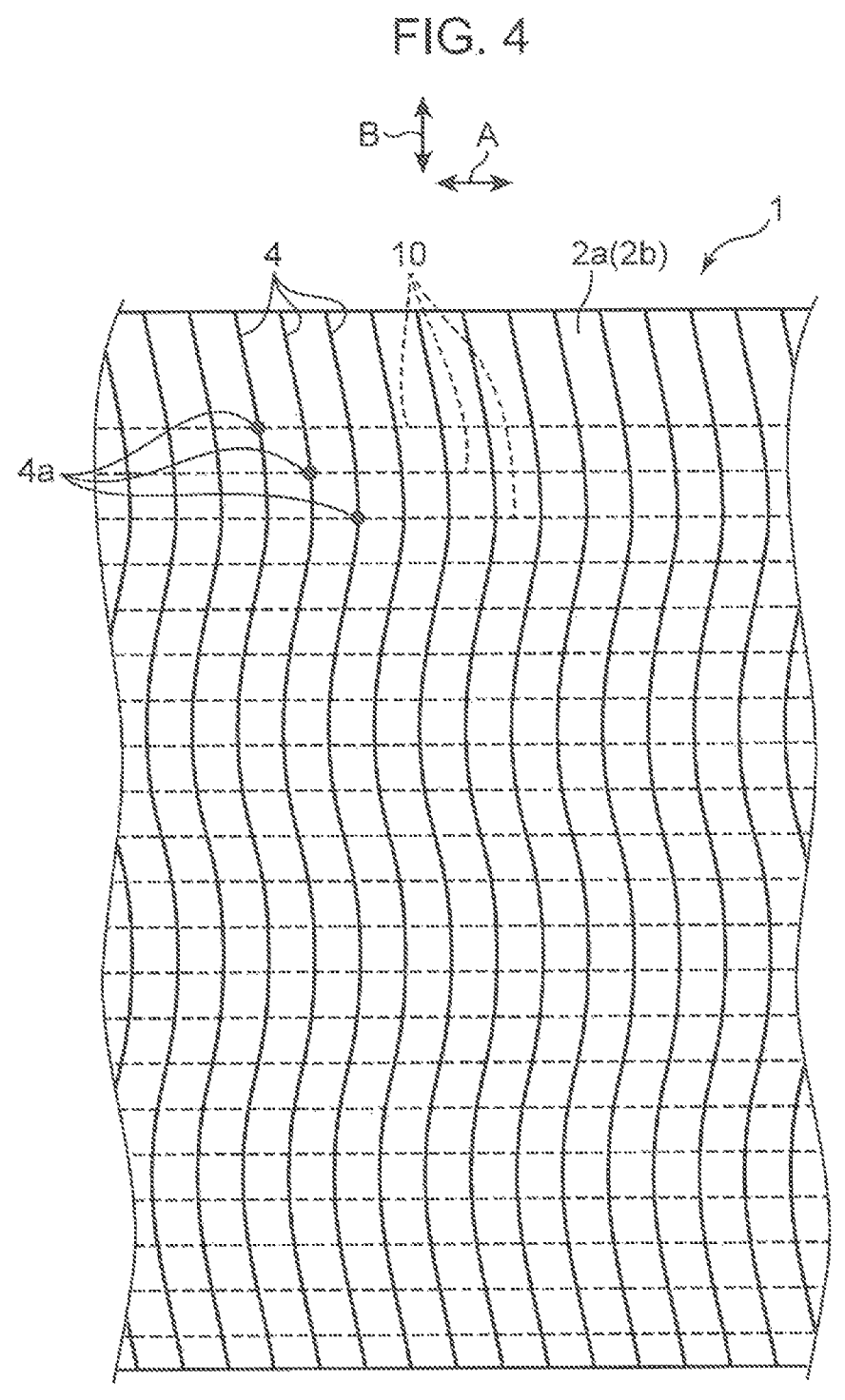
Figure 5:
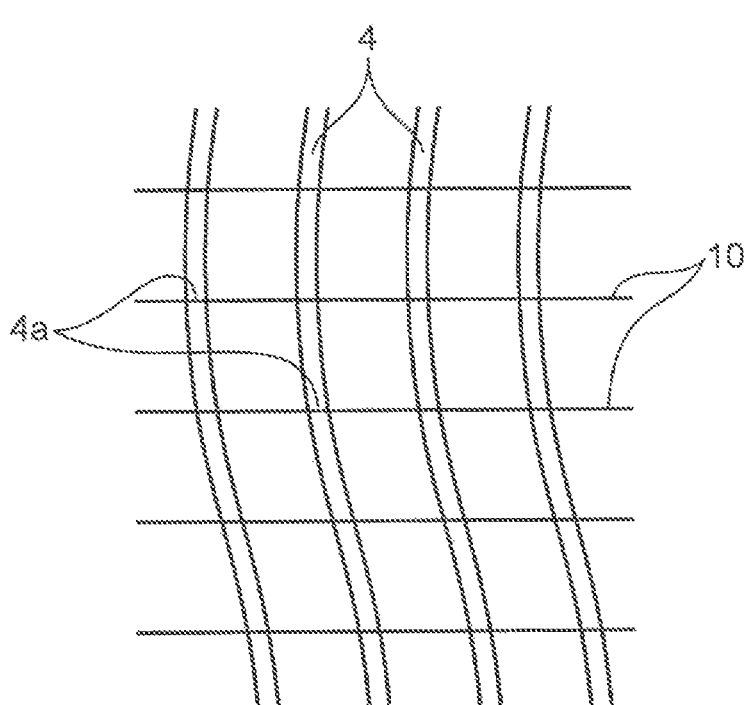
FIG. 5 is an enlarged view of a part of FIG. 1.

FIGS. 4 and 5 each schematically illustrate the bonding sections of FIG. 1. As illustrated in FIGS. 1, 4, and 5, the first bonding sections 4 are disposed at equal intervals in the longitudinal direction A of the sheets 2*a*, 2*b*, and continuously extend parallel to each other in the width direction B of the sheets 2*a*, 2*b*.

Each first bonding section 4 intersects all the elastic members 10 at positions of respective intersections 4*a* and extends along a line intersecting an extending direction (i.e., the longitudinal direction A) of the elastic members 10. Specifically, each first bonding section 4 extends between opposite outer portions of the sheets 2*a*, 2*b* in the width direction B across a region where the elastic members 10 are disposed.

At an intersection 4*a* where each of the elastic members 10 intersect the corresponding on one of the first bonding sections 4, each of the elastic members 10 and each of the sheets 2*a*, 2*b* are bonded to each other.

As illustrated in FIG. 1, each of the first bonding sections 4 has a wavy line shape extending in the width direction B while being periodically displaced in the longitudinal direction A with a convex portion 4*b* and a concave portion 4*c* that alternately appear continuously. Two adjacent first bonding sections 4 are disposed with convex portions 4*b* or concave portions 4*c* that at least partially overlap each other, and specifically are disposed with the convex portions 4*b* or the concave portions 4*c* that at least partially coincide in shape with each other. This enables a pleat in a wavy line shape to be conned along each of the first bonding sections 5 in a wavy line shape when the composite stretchable member 1 contracts. As a result, the composite stretchable member 1 has a plurality of pleats in a wavy line shape, thereby improving design properties of the composite stretchable member 1.

Specifically, two adjacent first bonding sections 4 illustrated in FIG. 1 are disposed with both the bonding sections 4 coinciding in phase with each other in the width, direction B in at least one region. For example, wavy lines in two adjacent first bonding sections 4 may be disposed side by side in the same phase over the entire length as illustrated in FIG. 1, but may be disposed side by side in the same phase only in some sections and in different phases in other sections.

Additionally, a first bonding section 4 in a wavy line shape may have a wavelength that is constant over the entire length as illustrated in FIG. 1 or the wavelength may change depending on a position in the first bonding section 4 in the width direction B.

Furthermore, the first bonding section 4 in a wavy line shape may have an amplitude that is constant over the entire length as illustrated in FIG. 1, or the amplitude may change depending on a position in the first bonding section 4 in the width direction B.

As described above, when at least one of the phase, the wavelength, and the amplitude is appropriately changed and set in a part or the whole of the plurality of first bonding sections 5 in a wavy line shape, a plurality of pleats in a wavy line shape formed when composite stretchable member 1 contracts can be partially or entirely changed in shape. As a result, the composite stretchable member 1 having a varied pattern can be formed.

When viewed from the width direction B, for example, when viewed from the arrow B1 in FIG. 1, the plurality of first bonding sections 4 is disposed at intervals that are set to have a space between two adjacent first bonding sections 4, being closed by the convex portion 4*b* of at least one of the two first bonding sections 4.

In the first bonding section 4, the sheets 2*a*, 2*b* as well as the sheets 2*a*, 2*b* and the elastic member 10 are bonded to each other by welding. In the present embodiment, these are ultrasonically welded.

The sheets 2*a*, 2*b* are bonded to each other by being partially melted and welded. In contrast, the elastic member 10 and the sheets 2*a*, 2*b* are welded to each other when the sheets 2*a*, 2*b* are partially melted and the covering layer 10*b* of the elastic member 10 is melted.

Specifically, in the present embodiment, a rubber thread having a melting point of about 200° C. is used as the rubber thread 10*a* contained in the elastic member 10, and the covering layer 10*b* is made of magnesium stearate (melting point: about 120° C.) having a lower melting point than the rubber thread. When the elastic member 10 and the sheets 2*a*, 2*b* are welded to each other, the covering layer 10*b* is melted to weld the covering layer 10*b* to the sheets 2*a*, 2*b* without melting of the rubber thread 10*a*.

(2) Manufacturing Apparatus for a Composite Stretchable Member

Next, a manufacturing apparatus for manufacturing the composite stretchable member 1 will be described.

Figure 6:
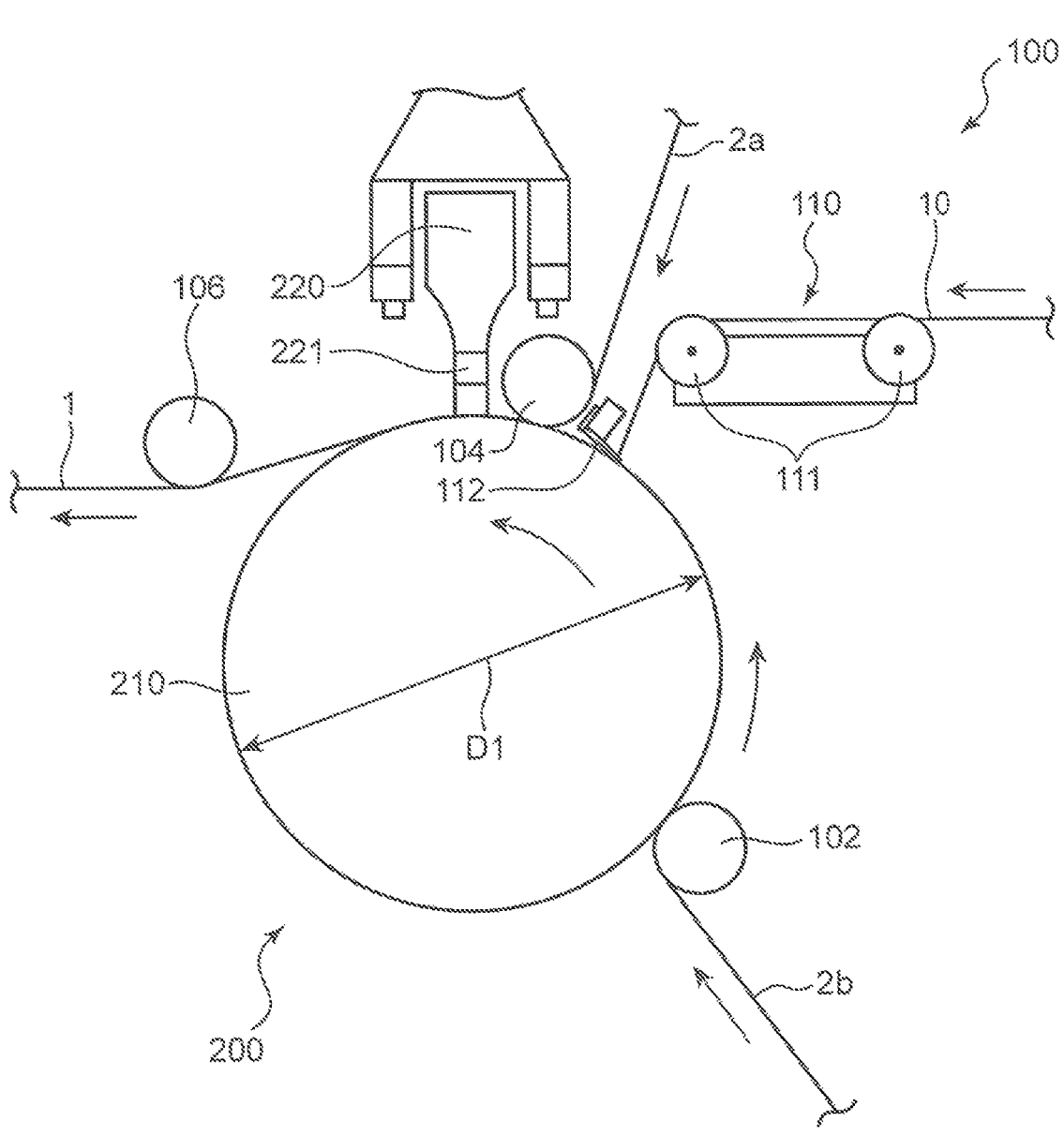
FIG. 6 is a schematic view illustrating a configuration of a manufacturing apparatus for manufacturing a composite stretchable member according to an embodiment of the present invention.

FIG. 6 is a schematic view of a manufacturing apparatus 100 according to an embodiment of the present invention.

The manufacturing apparatus 100 includes: a bonding device 200 that ultrasonically welds and bonds the elastic member 10 to the sheets 2*a*, 2*b*, and the sheets 2*a*, 2*b* to each other while the elastic member 10 is sandwiched between the sheets 2*a*, 2*b*; a first guide roller 102 that guides the lower sheet 2*b* to the bonding device 200 (specifically, an anvil roll 210 described later); an elastic member guide device (guide device) 110 that supplies the elastic member 10 to the bonding device 200; a nip roll (second guide roller) 104 that guides the upper sheet 2*a* to the bonding device 200 and presses the two sheets 2*a*, 2*b*, and the elastic member 10; and a third guide roller 106 that guides a bonded sheet or the like, i.e., the composite stretchable member 1.

The bonding device 200 includes the anvil roll (conveying roller) 210 and a horn (compressing device) 220.

The anvil roll 210 is a rotating member that rotates about an axis extending in a direction orthogonal to the paper surface of FIG. 6. Hereinafter, the direction orthogonal to the paper surface of FIG. 6 is referred to as a "front-back direction". The anvil roll 210 is rotatably attached to a rotation shaft, as a rotation center, extending horizontally (in the front-back direction) with respect to a vertical wall portion of an apparatus, such as a panel (not illustrated). The anvil roll 210 rotates to convey the elastic member 10 guided by the elastic member guide device 110 while the elastic member 10 is sandwiched between the sheets 2*a*, 2*b* guided by the rollers 102 and 104, respectively, on the outer peripheral surface of the anvil roll 210. In the example illustrated in FIG. 6, the anvil roll 210 rotates counterclockwise in FIG. 6. Hereinafter, the sheets 2a, 2b sandwiching the elastic member 10 is referred to as pre-bonding sheets.

Figure 11:
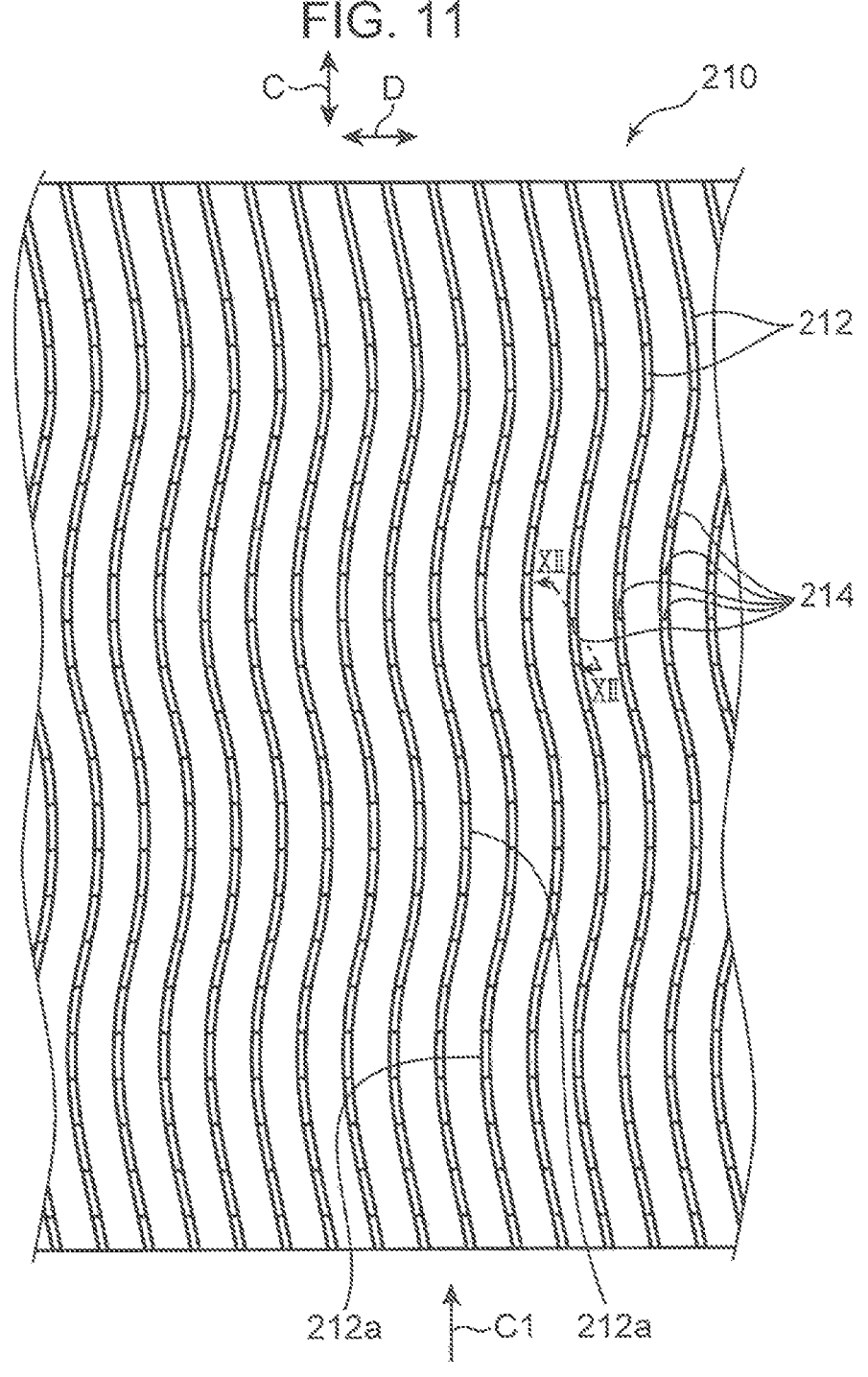
FIG. 11 is a view illustrating an outer peripheral surface of the anvil roll of FIG. 6.

As illustrated in FIG. 11, the outer peripheral surface of the anvil roll 210 is provided with a protrusion 212 protruding radially outward. The protrusion 212 is provided on the outer peripheral surface of the anvil roll 210 over the entire width in its rotation axis direction C. The protrusion 212 has a wavy line shape corresponding to the first bonding section 4 of the composite stretchable member 1.

That is, a plurality of protrusions 212 in a wavy line shape extends along the rotation axis direction C of the anvil roll 210, and the protrusions 212 are disposed parallel to each other and at equal intervals in a circumferential direction D.

The plurality of protrusions 212 in a wavy line shape is disposed at intervals, corresponding to the shape of the plurality of first bonding sections 4 of the composite stretchable member 1 described above. The intervals are set such that when viewed from the rotation axis direction C of the anvil roll 210, e.g., when viewed from the arrow C1 in FIG. 11, a space between two adjacent protrusions 212 is closed by a convex portion 212a (a convex portion protruding in the circumferential direction D) of at least one of the two adjacent protrusions 212, the convex portion 212a corresponding to the convex portion 4b of the first bonding section 4. Thus, causing an output unit 221, which is described later, of a horn 220 to face the plurality of protrusions 212 in a wavy line shape of the anvil roll 210 enables the sheets 2a, 2b to be reliably sandwiched between the output unit 221 and the protrusions 212 during ultrasonic welding. As a result, when the plurality of first bonding sections 4 of the composite stretchable member 1 of FIG. 1 is formed by ultrasonic welding, fluctuations in pressure when the two sheets 2a, 2b are sandwiched between the output unit 221 of the horn 220 and the protrusions 212 in a wavy line shape of the anvil roll 210 (see FIG. 12) can be reduced at any position in the composite stretchable member 1 in the width direction B (i.e., the rotation axis direction C of the anvil roll 210).

Figure 12:
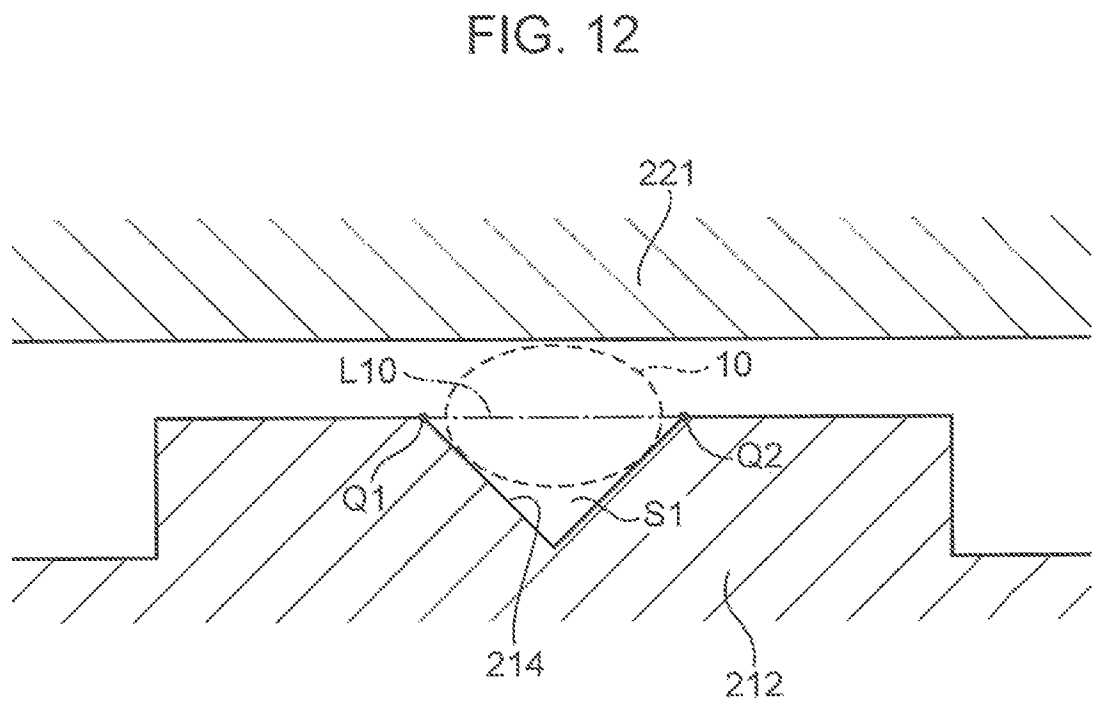

As illustrated in FIGS. 11 and 12, a plurality of grooves 214 recessed radially inward of the anvil roll 210 is formed in each protrusion 212 in a wavy line shape. The plurality of grooves 214 is disposed at equal intervals in the rotation axis direction C each protrusion 212. The grooves 214 of each of adjacent protrusions 212 are disposed side by side at equal intervals in the circumferential direction D of the anvil roll 210.

Into each of the grooves 214, a portion of the lower sheet 2b (a sheet disposed close to the anvil roll 210) with the elastic member 10 disposed is inserted. Thus, placement of the elastic members 10 for the first bonding section 4 coincides with placement of the grooves 214 for the protrusion 212.

Figure 7:
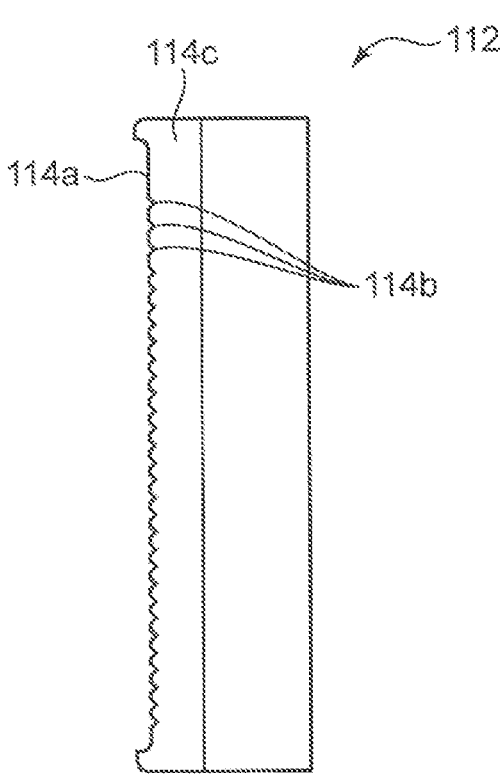
FIG. 7 is a plan view of the guide plate of FIG. 6.

The sheet 2b is conveyed by the anvil roll 210 while having a portion where the elastic member 10 is disposed, the portion being inserted into the corresponding one of the grooves 214. As described above, in the present embodiment, the elastic members 10 are guided into the corresponding grooves 214 by a guide plate 112 provided with guide grooves 114b (see FIG. 7) at positions corresponding to the respective grooves 214, so that the elastic members 10 are each stably disposed at an appropriate position on the sheet 2b.

In the present embodiment, the sheet 2b together with the elastic members 10 that are partially inserted into the corresponding grooves 214 are conveyed by the anvil roll 210. Only the sheet 2b with portions inserted into the grooves may be conveyed.

The grooves 214 are formed in the protrusion 212 at portions where the respective elastic members 10 are disposed as described above, so that at least a part of each of the elastic members 10 disposed on a pre-bonding sheet is retracted in the corresponding grooves when the pre-bonding sheet is compressed during bonding. Thus, an elastic member 10 is prevented from being cut when being compressed.

However, when the groove 214 has an excessive sectional area, the elastic member 10 may be less likely to be appropriately bonded to the sheets 2a, 2b. Thus, in the present embodiment, as illustrated in FIG. 12, when the elastic member 10 with a natural length is disposed in the groove 214, a part of the elastic member 10 protrudes outward from the groove 214, and the rest of the elastic member 10 is accommodated in the groove 214. Specifically, the groove 214 is configured to have a section taken along a plane substantially orthogonal to the circumferential direction (conveying direction) of the anvil roll 210, the section having a shape in which when the elastic member 10 is disposed in the groove 214 with the natural length, a part of the elastic member 10 protrudes outward in the radial direction of the anvil roll 210 front a linear imaginary line L10 connecting open ends (Q1, Q2) of the groove 214. The groove 214 is also configured to have the sectional shape in which when the elastic member 10 is extended from a natural state (e.g., when being elongated 300%) is disposed in the groove 214, a part of the elastic member 10 protrudes outward in the radial direction of the anvil roll 210 from the linear imaginary line L10 connecting the open ends (Q1, Q2) of the groove 214. The groove 214 described above preferably has a sectional shape of a substantially V-shape as illustrated in FIG. 12. The groove 214 described above preferably has a sectional area S1 smaller than a sectional area of the elastic member 10 to be disposed.

Figures 10A, 10B:
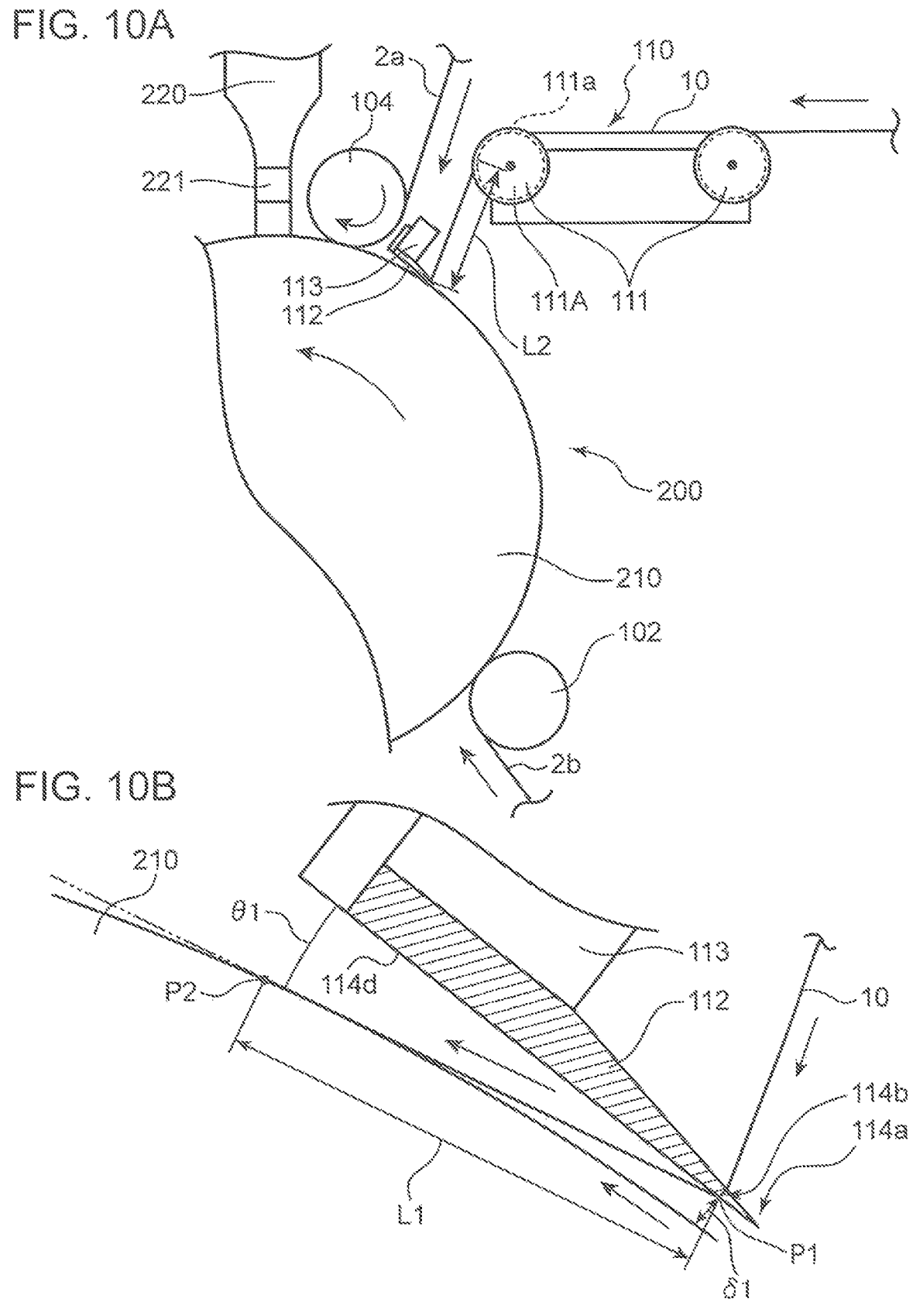
FIG. 10A is an enlarged view of the guide plate and a peripheral portion thereof of the manufacturing apparatus of FIG. 6.
FIG. 10B is an enlarged view of a portion where an elastic member is fed from a guide groove of the guide plate of FIG. 10A to an anvil roll.

The horn 220 illustrated in FIGS. 6 and 10A is a device that applies ultrasonic vibration to a pre-bonding sheet conveyed by the anvil roll 210 while compressing (pressurizing while sandwiching) the pre-bonding sheet with the outer peripheral surface of the anvil roll 210. The horn 220 is disposed to face the outer peripheral surface of the anvil roll 210. In the example of FIG. 6, the horn 220 is disposed to face an upper portion of the outer peripheral surface of the anvil roll 210. The horn 220 is provided at its leading end with an output unit 221 that applies ultrasonic vibration toward the outer peripheral surface of the anvil roll 210.

The horn 220 applies ultrasonic vibration to a pre-bonding sheet with the output unit 221 pressing against the pre-bonding sheet and compressing the pre-bonding sheet together with the anvil roll 210. This causes the sheets 2a, 2b to be melted and welded to each other. The elastic member 10 is also melted, so that the elastic member 10 and the sheets 2a, 2b are welded to each other. Specifically, the output unit 221 compresses the pre-bonding sheet together with the protrusion 212, and bonds the sheets 2a, 2b to each other and bonds the elastic member 10 to the sheets 2a, 2b in a portion of the pre-bonding sheet disposed on the protrusion 212. The leading end of the output unit 221 has a planar shape (See FIG. 12).

As described above, in the present embodiment, the covering layer 10b is made of magnesium stearate having a lower melting point than the rubber thread 10a. Thus, during welding between the elastic member 10 and the sheets 2a, 2b, the covering layer 10b is melted to weld the covering layer 10b to the sheets 2a, 2b without melting of the rubber thread 10a.

The output unit 221 at the leading end of the horn 220 extends in the front-back direction (the rotation axis direction C of the anvil roll 210), and the horn 220 applies ultrasonic vibration to the outer peripheral surface of the anvil roll 210 throughout in the rotation axis direction C of the anvil roll 210. While a pre-bonding sheet is conveyed by the anvil roll 210, the horn 220 always applies ultrasonic vibration. Thus, as the pre-bonding sheet is conveyed by the anvil roll 210, the pre-bonding sheet is continuously bonded.

As illustrated its FIG. 6, in the present embodiment, the lower sheet 2b is guided by the first guide roller 102 to a position separated upstream in the conveying direction (the right side in FIG. 6) from the horn 220 on the outer peripheral surface of the anvil roll 210. The sheet 2b is conveyed toward the horn 220 along the outer peripheral surface of the anvil roll 210 along with rotation of the anvil roll 210.

The upper sheet 2a is introduced into a portion of the outer peripheral surface of the anvil roll 210, being near the horn 220 and upstream of the horn 220 in the conveying direction (the right side in FIG. 6), by the nip roll 104.

The elastic member 10 is introduced onto the outer peripheral surface of the anvil roll 210 at a position between a position where the sheet 2b is introduced onto the anvil roll 210 and a position where the sheet 2a is introduced onto the anvil roll 210 by the elastic member guide device 110. As a result, the elastic member 10 is conveyed to a position facing the horn 220 while being sandwiched between the sheets 2a, 2b.

Although the sheet 2a may be introduced onto the anvil roll 210 from the nip roll 104 at any position between a position where the elastic member 10 is introduced and a position facing the horn 220, the position is preferably on a side close to the position facing the horn 220, and more preferably near the position facing the horn 220. In the present embodiment, as illustrated in FIGS. 6 and 10A, the nip roll 104 is disposed at a position closest upstream in the conveying direction (the right side in FIGS. 6 and 10A) of the horn 220 in the conveying direction of the sheets 2a, 2b, i.e., the rotation direction of the anvil roll 210 (counterclockwise direction in FIG. 10A). This configuration enables preventing the elastic member 10 introduced onto the outer peripheral surface, of the anvil roll 210 from being covered with the sheet 2a at an early stage and from causing positional deviation.

The elastic members 10 are introduced onto the outer peripheral surface of the anvil roll 210 while being arranged parallel to each other in the front-back direction, and are placed on the sheet 2, which is previously introduced onto the outer peripheral surface of the anvil roll 210, parallel to each other in the width direction B, on the outer peripheral surface of the anvil roll 210. The elastic members 10 are each introduced onto the anvil roll 210 while being elongated in the circumferential direction D of the anvil roll 210. In the present embodiment, the elastic members 10 are each introduced onto the anvil roll 210 while being elongated 300% of the natural state when the natural state is set to 100%.

As illustrated in FIGS. 6, 10A, and 10B, the elastic member guide device 110 includes a plurality of guide rollers 111 and a guide plate 112 in a plate-like shape as a guide member.

Each of the guide rollers 111 is a rotary member rotatable about its axis extending in the front-back direction, and guides the elastic member 10 toward the anvil roll 210 while the elastic member 10 is elongated (e.g., elongated 300%).

As illustrated in FIGS. 6 to 10A and 10B, the guide plate 112 is a tabular member that guides the elastic members 10 to the corresponding grooves 214 (see FIGS. 11 and 12) formed on the outer peripheral surface of the anvil roll 210 while the elastic members 10 are separated from each other in the front-back direction, i.e., in a direction parallel to the axis of the anvil roll 210.

The guide plate 112 has a leading end 114a, which is an edge closest to the outer peripheral surface of the anvil roll 210, and a proximal end disposed farther away from the anvil roll 210 than the leading end 114a. The guide plate 112 is disposed to extend not only in a direction of coming into contact with and separating from the anvil roll 210 but also in the front-back direction. In the present embodiment, to prevent the guide plate 112 from interfering with the sheets 2a, 2b, the guide plate 112 has a thickness t (dimension in a vertical direction illustrated in FIG. 8) that is set to be small, and has a thin plate shape.

Figure 8:
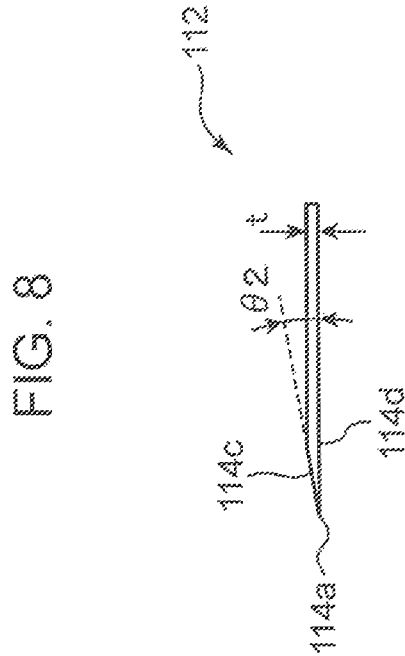
FIG. 8 is a side view of the guide plate of FIG. 7.

The leading end 114a of the guide plate 112 has a tapered shape. Specifically, as illustrated in FIG. 8, the guide plate 112 is provided in its leading end portion (portion close to the anvil roll 210) with an inclined surface 114c that is inclined toward the leading end 114a to approach a bottom surface 114d of the guide plate 112. The inclined surface 114c and the bottom surface 114d form the leading end 114a tapered. In the present embodiment, the inclined surface 114c and the bottom surface 114d form an angle θ2 that is set to be a small angle.

As illustrated in FIGS. 10A and 10B, the leading end 114a of the guide plate 112 is disposed upstream in the conveying direction (right side in FIGS. 10A and 10B) of a contact point P2 at which the guide plate 112 is in contact with the elastic member 10 on the outer peripheral surface of the anvil roll 210 in the rotation direction (counterclockwise direction in FIGS. 10A and 10B) of the anvil roll 210 while facing upstream in the conveying direction.

Figure 9:
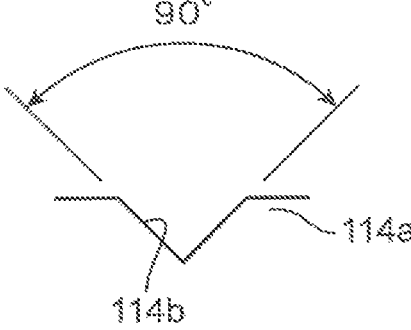
FIG. 9 is an enlarged view of a guide groove of the guide plate of FIG. 7.

The leading end 114a tapered of the guide plate 112 is provided with a plurality of guide grooves 114b. Specifically, the guide grooves 114b are formed at respective positions away from each other at equal intervals in the front-back direction (direction parallel to the axis of the anvil roll 210) at the leading end 114a of the guide plate 112, and individually hold the respective elastic members 10 to guide the elastic members 10 into the respective grooves 214 of the anvil roll 210. As illustrated in FIG. 9 that illustrates a part of the guide grooves 114b in FIG. 7 in an enlarged manner, each of the guide grooves 114b is recessed from the leading end 114a of the inclined surface 114c toward the proximal end, and has a V-shape having an opening angle of about 90 degrees. These guide grooves 114b reliably position and hold the respective elastic members 10 to guide the elastic members 10 onto the outer peripheral surface of the anvil roll 210 while separating the elastic members 10 from each other in the front-back direction. The guide grooves 114b face the respective grooves 214 formed in the anvil roll 210 and are provided at the same intervals as the grooves 214 to guide the elastic members 10 into the respective grooves 214.

The leading end 114a of the guide plate 112 and the guide grooves 114b formed at the leading end 114a face in an opposite direction (i.e., a clockwise direction) to the rotation direction of the anvil roll 210 (the counterclockwise direction in FIGS. 6 and 10A). Thus, the elastic members 10 engaged into the respective guide grooves 114b are pulled by the anvil roll 210 rotating in the counterclockwise direction, and are bent at bottoms P1 of the respective guide groove 114*b*. Each of the elastic members 10 then extends in a tangential direction of the contact P2 on the outer peripheral surface of the anvil roll 210, and is inserted into the corresponding one of the grooves 214 (see FIGS. 11 and 12) at the contact P2 on the outer peripheral surface of the anvil roll 210.

As illustrated in FIGS. 10A and 10B, as a length L1 (specifically, a distance L1 from the bottom P1 of a guide groove 114*b* to the contact point P2 at which an elastic member 10 is in contact with the anvil roll 210) of the elastic member 10 positioned between the guide groove 114*b* and a groove 214 of the anvil roll 210 decreases in the guide plate 112, a defect in which the elastic member 10, such as a rubber thread, is detached from the groove 214 of the anvil roll 210 is reduced.

As illustrated in FIG. 10B, the guide plate 112 is disposed with a gap δ1 between the bottom P1 of the guide groove 114*b* and the outer peripheral surface of the protrusion 212 of the anvil roll 210, the gap δ1 being as small as possible. This enables the length L1 of the elastic member 10 to be further shortened, so that the defect in which the elastic member 10 is detached from the groove. 214 of the anvil roll 210 is further reduced.

As illustrated in FIG. 10B, the guide plate 112 is disposed with the bottom surface 114*d* facing the anvil roll 210 that forms an acute angle θ1 (90 degrees or less) with respect to a tangent line of the anvil roll 210 at the contact point P2 where the anvil roll 210 and the elastic member 10 are in contact with each other. This enables further shortening a length L1 of the elastic member 10, and further reducing the defect in which the elastic member 10 is detached from the groove 214 of the anvil roll 210.

As illustrated in FIGS. 6 and 10A, the plurality of guide rollers 111 are disposed upstream in the conveying direction of the guide plate 112 in the conveying direction of the elastic member 10 to guide the elastic member 10 into the guide groove 114*b*. Each of the guide rollers 111 is provided in its outer peripheral surface with grooves (not illustrated) away from each other in an extending direction of a rotation shaft of the guide roller 111 to guide the elastic members 10 into the respective guide grooves 114*b*.

As illustrated in FIG. 10A, a guide roller 111A positioned most downstream of the plurality of guide rollers 111 is disposed to be able to ensure some distance L2 in which the elastic member 10 is separated from the guide roll from the guide roller 111 and inserted into the guide groove 114*b* to prevent influence due to rotation unevenness and rattling of the guide roller 111A (e.g., slack of the elastic member 10 and the like). This configuration enables eliminating influence on the elastic member 10 due to rotation unevenness and rattling of the guide roller 111, such as a slack of the elastic member 10.

As illustrated in FIGS. 6 and 10A, the nip roll 104 is disposed upstream in the conveying direction of the horn 220. The nip roll 104 can sandwich two sheets and the elastic member 10 in cooperation with the anvil roll 210 in a region where the elastic member 10 is inserted into the groove 214 of the anvil roll 210, i.e., a section from a first position a contact point between the anvil roll 210 and the elastic member 10) P2 (see FIG. 10B) where the elastic member 10 is inserted into the groove 214 in the outer peripheral surface of the anvil roll 210 to the output unit 221 (see FIG. 10A) of the horn 220.

(3) Wearing Article and Method for Manufacturing the Same

Figure 13:
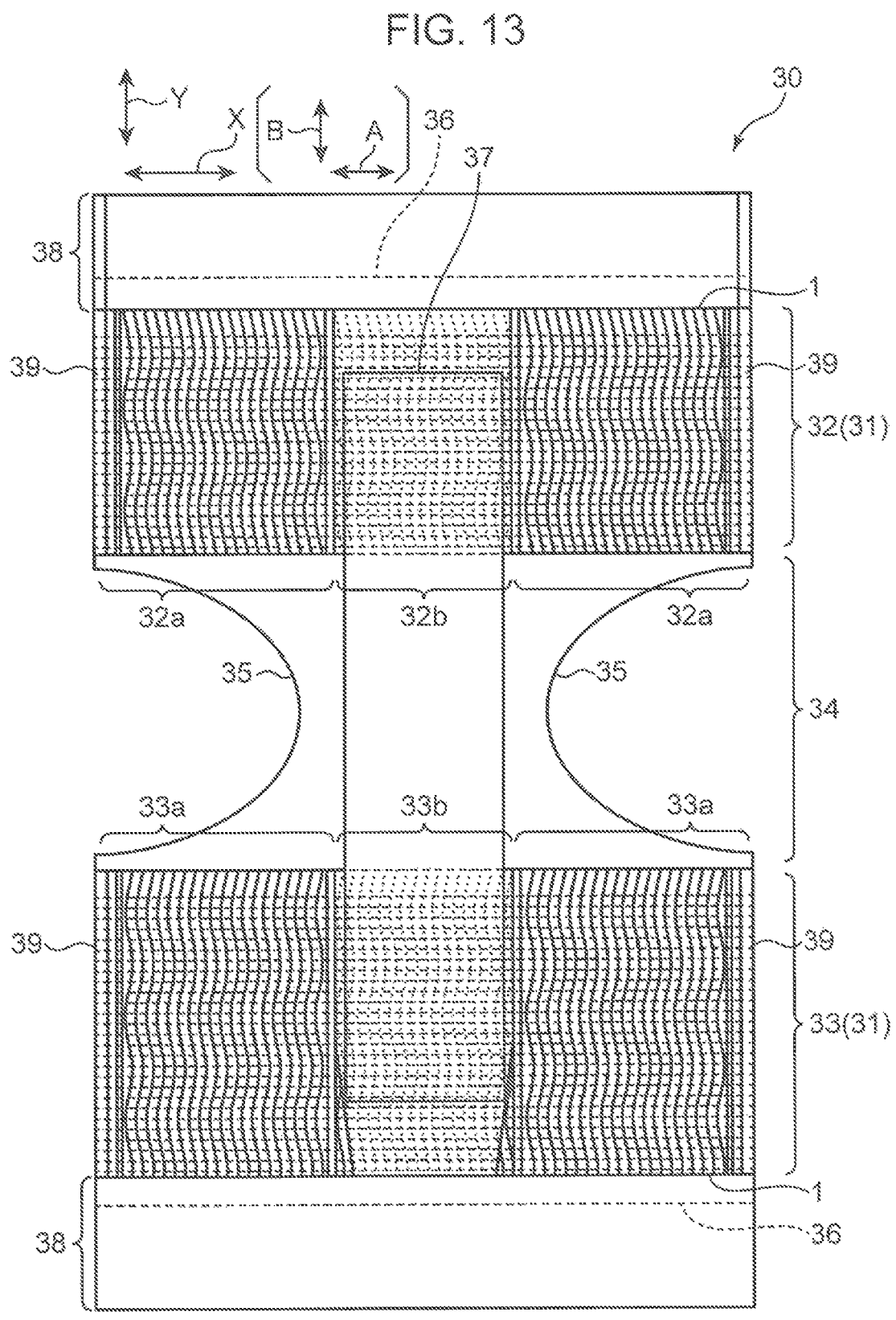
FIG. 13 is a developed view of a disposable diaper using a composite stretchable member.
Figure 14:
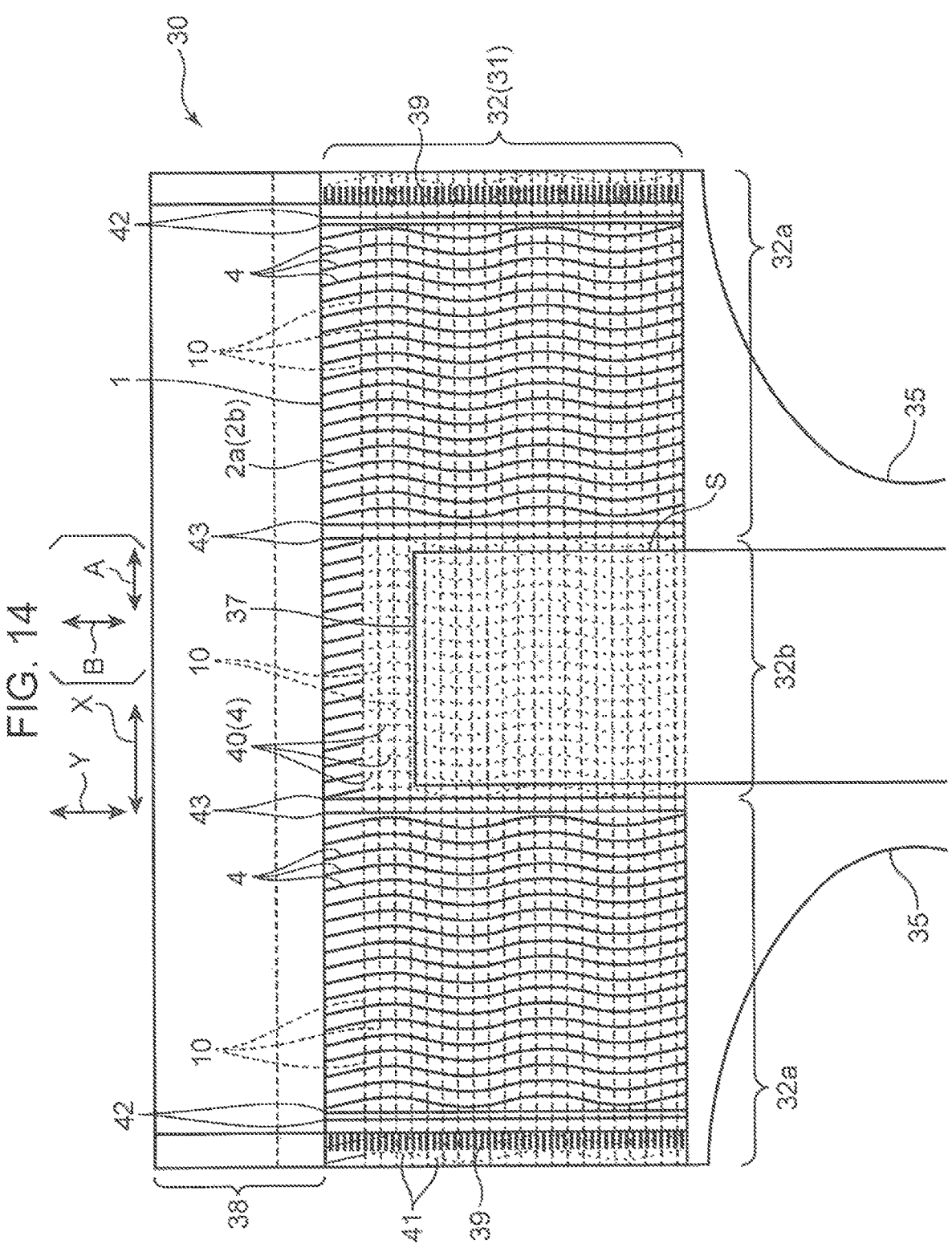
FIG. 14 is an enlarged plan view illustrating a front abdomen portion of the disposable diaper of FIG. 13.

FIGS. 13 and 14 are each a schematic view illustrating a disposable diaper (wearing article) 30 using the composite stretchable member 1 as a usage example of the composite stretchable member 1 configured as described above.

FIGS. 13 and 14 each illustrate a disposable diaper 30 that has an underpants-type form, and that mainly includes a waistline portion 31 formed of the composite stretchable member 1 having elasticity, a crotch portion 34, and an absorbent body 37 capable of absorbing liquid such as moisture.

The composite stretchable member 1 of the present embodiment is disposed in the waistline portion 31 with the longitudinal direction A of the composite stretchable member 1 aligning with a waistline direction X of the waistline portion 31. In other words, the composite stretchable member 1 is applied to a front abdomen portion 32 and a rear back portion 33 such that the extending direction of the composite stretchable member 1 (longitudinal direction A of the composite stretchable member 1) aligns with the waistline direction X (left-right direction in FIG. 13) at the time of wearing. That is, the waistline portion 31 includes the front abdomen portion 32 and the rear back portion 33, and is formed in an annular shape by joining the front abdomen portion 32 to the rear back portion 33 with a pair of joining regions 39.

FIG. 13 illustrates an unfolded state in which the disposable diaper 30 includes the front abdomen portion 32 constituting a front body of the waistline portion 31, the rear back portion 33 constituting a back body of the waistline portion 31, the crotch portion 34 constituting a crotch portion, and the absorbent body 37. The crotch portion 34 joins the front abdomen portion 32 to the rear back portion 33. The absorbent body 37 is disposed across the front abdomen portion 32, the crotch portion 34, and the rear back portion 33. Specifically, the absorbent body 37 is fixed to the front abdomen portion 32 and the rear back portion 33 while partially overlapping the front abdomen portion 32 and the rear back portion 33 formed of the composite stretchable member 1 to form overlapped portions S.

A folded portion 38 folded at a folding line 36 is continuously provided at an upper end of the front abdomen portion 32 and at a lower end of the rear back portion 33. The crotch portion 34 is provided with leg holes 35 that are each a substantially semicircular hole into which a leg can be inserted.

The front abdomen portion 32 includes stretchable regions 32*a* on both left and right sides, having elasticity that allow stretching in the waistline direction X, and a weakened region 32*b* in a central portion in which elasticity is weakened, the stretchable regions 32*a* on both the left and right sides and the weakened region 32*b* in the central portion being continuously formed. As with the front abdomen portion 32, the rear back portion 33 also includes stretchable regions 33*a* on both left and right sides, having elasticity that allow stretching in the waistline direction X, and a weakened region 33*b* in a central portion in which elasticity is weakened, the stretchable regions 33*a* on both the left and right sides and the weakened region 33*b* in the central portion being continuously formed. The weakened region 32*b* at the front and the weakened region 33*b* at the rear may be formed at least in the overlapped portions S of the absorbent body 37 and the front abdomen portion 32, and of the absorbent body 37 and the rear back portion 33, respectively, and may be formed in a range wider than each of the overlapped portions S as illustrated in FIGS. 13 and 14. The weakened regions 32*b* and 33*b* formed wider than the overlapped portions S enable an attachment error of the absorbent body 37 to be absorbed.

The composite stretchable member 1 is formed by sandwiching the elastic members 10 between front and back surfaces of the corresponding sheets 2a, 2b paired and ultrasonically welding the elastic members 10 and the sheets 2a, 2b to each other in the entire range (i.e., a range of the entire stretchable regions 32a, 33a and weakened regions 32b, 33b) of the front abdomen portion 32 and the rear back portion 33 in FIG. 13. That is, as illustrated in FIG. 14, while the elastic members 10 being extended in the waistline direction X (longitudinal direction A) are sandwiched between the sheets 2a, 2b paired, the elastic members 10 and the sheets 2a, 2b paired are ultrasonically welded to each other at the first bonding sections 4 in a wavy line shape, being separated from each other in the waistline direction X (longitudinal direction A).

The composite stretchable member 1 in FIGS. 13 and 14 includes portions other than the front abdomen portion 32 and the rear back portion 33, such as the crotch portion 34 and the folded portion 38 that are formed of the sheet 2a of the sheets 2a, 2b paired (a sheet body constituting an outer side of the disposable diaper 30 in the form of a disposable diaper).

Like the weakened region 32b of the front abdomen portion 32 illustrated in FIG. 14, each of the elastic members 10 in the present embodiment is cut to form the weakened region 32b in which the elasticity of the elastic members 10 is weakened in a range including the overlapped portion S where the absorbent body 37 overlapped with the composite stretchable member 1. Although each elastic member 10 may be cut at one place at least, each elastic member 10 is cut at a plurality of places at equal intervals in the longitudinal direction A, for example.

The weakened region 32b includes a first bonding section 4 in a wavy line shape that is formed of a dotted-line bonding section 40 including a plurality of points without intersecting the elastic member 10, being scattered in the wavy line shape. The dotted-line bonding section 40 bonds the two sheets 2a, 2b to each other by ultrasonic welding or the like, but does not bond the sheets 2a, 2b to the elastic member 10. Thus, the first bonding section 4 formed of the dotted-line bonding section 40 is disposed without forming the intersection 4a with the elastic member 10, and the elastic member 10 is disconnected by cutting, in a range of the weakened region 32b including the overlapped portion S overlapping the absorbent body 37 in the composite stretchable member 1.

The disposable diaper 30 illustrated in FIGS. 13 and 14 includes the front abdomen portion 32 and the rear back portion 33 that are each provided at its opposite ends in the waistline direction X with the respective joining regions 39 to join the opposite ends of the front abdomen portion 32 to the opposite ends of the rear back portion 33. Each joining region 39 extends linearly in the width direction B.

The joining region 39 includes at least partially a non-formation region where the intersection 4a (see FIG. 1) of the first bonding section 4 and the elastic member 10 is not formed. Thus, the joining region 39 in the disposable diaper 30 has no elasticity. The joining regions 39 of the front abdomen portion 32 and those of the rear back portion 33 are bonded to each other by ultrasonic welding or the like. Then, the elastic member 10 may be bonded to the sheets 2a, 2b, but may not necessarily be bonded to the sheets 2a, 2b.

FIG. 14 illustrates a region outside each joining region 39 in the waistline direction (width direction) X. Although in the region, the sheets 2a, 2b are bonded to each other with a dotted-line bonding section 41 formed of a plurality of points dotted in a wavy line shape, the sheets 2a, 2b are not bonded to the elastic member 10.

As illustrated in FIG. 14, the disposable diaper 30 of the present embodiment includes at least one second bonding section 42 that linearly extends in the width direction B of the composite stretchable member 1, i.e., a width direction Y of the waistline portion 31, and that is formed between the joining region 39 and the first bonding section 4 closest to the joining region 39. FIG. 14 illustrates an example in which a plurality of (two) second bonding sections 42 are formed side by side in the waistline direction X.

In the present embodiment, the weakened region 32b including the overlapped portion S has an edge extending linearly in the width direction Y. Between the weakened region 32b including the overlapped portion S and the first bonding section 4 closest to the weakened region 32b (overlapped portion S), at least one third bonding section 43 linearly extending in the width direction B is formed.

The disposable diaper 30 configured as described above is manufactured as follows.

First, a continuous body, in which the crotch portion 34 is integrated with a pair of composite stretchable members 1 for forming the front abdomen portion 32 and the rear back portion 33 of the waistline portion 31, is prepared.

When the composite stretchable member 1 illustrated in FIGS. 13 and 14 is manufactured, not only the plurality of first bonding sections 4 in a wavy line shape, but also dotted-line bonding sections 40 in the weakened regions 32b, 33b, dotted-line bonding sections 41, the second bonding sections 42 in a linear shape, and third bonding sections 43 near the weakened regions 32b, 33b, are required to be continuously formed in the composite stretchable member 1 for performing ultrasonic welding. Thus, the outer peripheral surface of the anvil roll 210 is provided with not only the protrusion 212 (see FIG. 11) corresponding to the first bonding section 4 in a wavy line shape, but also protrusions having shapes corresponding to the dotted-line bonding sections 40, 41, the second bonding section 42, and the third bonding section 43. Then, the ultrasonic welding is performed using the anvil roll 210 having the plurality of types of protrusion described above.

After the ultrasonic welding, the composite stretchable member 1 is subjected to a weakening process in which the elastic members 10 in the weakened regions 32b, 33b are cut so as not to expand and contract in the weakened regions.

After the leg hole 35 is formed in the crotch portion 34, the crotch portion 34 is folded in half at an intermediate position of the crotch portion (an intermediate position in the width direction Y orthogonal to the waistline direction X) to allow the crotch portion 34 to be positioned inside.

Then, the joining regions 39 at the opposite ends of the front abdomen portion 32 in the waistline direction X and the joining regions 39 at the opposite ends of the rear back portion 33 therein are bonded to each other by the ultrasonic welding to form side seals, thereby forming a shape of the disposable diaper 30. After that, when the disposable diaper 30 is separated from an adjacent continuous body of a pair of composite stretchable members 1, the disposable diaper 30 is completed.

Features of the Present Embodiment (1)

The composite stretchable member 1 of the present embodiment includes the two sheets 2a, 2b facing each other, and the plurality of elastic members 10 extending along the longitudinal direction A so as to be stretchable in the longitudinal direction A between the sheets 2a, 2b. The sheets 2a, 2b are bonded to each other at the plurality of first bonding sections 4. Each first bonding section 4 continuously extends along the width direction B intersecting the longitudinal direction A and intersects the plurality of elastic members 10. Each elastic member 10 is bonded to each of the sheets 2a, 2b at the intersection 4a with the corresponding one of the first bonding sections 4. Each first bonding section 4 has a wavy line shape extending in the width direction B with the convex portions 4b and the concave portions 4c that alternately appear continuously. Two of the first bonding sections 4, being adjacent to each other, are at least partially (entirely in the first bonding section 4 in the present embodiment) disposed with the convex portions 4b overlapping each other or the concave portions 4c overlapping each other when viewed from the longitudinal direction A.

This configuration causes pleats in a wavy line shape to be formed along the respective first bonding sections 4 in a wavy line shape when the composite stretchable member 1 contracts, and thus enables a unique texture to be expressed by the composite stretchable member 1. As a result, the disposable diaper 30 of the present embodiment can be manufactured as a wearing article having high design properties using the composite stretchable member 1.

(2)

The composite stretchable member 1 of the present embodiment includes two adjacent first bonding sections 4 that are disposed with both the bonding sections 4 coinciding in phase with each other in the width direction B in at least one region. This configuration enables forming a plurality of pleats in a wavy line shape coinciding in phase when the composite stretchable member 1 contracts, and thus enables manufacturing the disposable diaper 30 (wearing article) having higher design properties.

(3)

The composite stretchable member 1 of the present embodiment includes the plurality of first bonding sections 4 disposed at intervals that are set to have a space between two adjacent first bonding sections 4, being closed by the convex portion 4b of at least one of the two first bonding sections 4 when viewed from the width direction B. This configuration causes the convex portion 4b of any one of the two first bonding sections 4 to exist between the two adjacent first bonding sections 4 when viewed from the width direction B, so that fluctuations in pressure when the two sheets 2a, 2b are sandwiched between the protrusions 212 of the anvil roll 210 and the output unit 221 of the horn 220 to form the plurality of first bonding sections 4 can be reduced at any position in the width direction B, and thus the first bonding sections 4 without unevenness (specifically, unevenness in height and adhesion strength of the first bonding sections 4) can be formed. This configuration also enables reducing vibrations of the anvil roll 210, the horn 220, and the like, which are means for applying pressure to the two sheets 2a, 2b to form the first bonding sections 4.

The disposable diaper 30, which is a wearing article of the present embodiment, includes the waistline portion 31 to be disposed around a waistline of a wearer. At least a part of the waistline portion 31 is formed of the composite stretchable member 1 of the present embodiment. As a result, pleats in a wavy line shape are formed along each first bonding section 4 as described above, and a unique texture is expressed by the composite stretchable member 1. This enables manufacturing the disposable diaper 30 having high design properties.

The disposable diaper 30, which is a wearing article of the present embodiment, includes the waistline portion 31 having the front abdomen portion 32 disposed on the front of the abdomen of a wearer and the rear back portion 33 disposed on the buttocks of the wearer. The waistline portion 31 is formed in an annular shape by joining the front abdomen portion 32 to the rear back portion 33 with the pair of joining regions 39. The front abdomen portion 32 and the rear back portion 33 are formed of the composite stretchable member 1. The composite stretchable member 1 is disposed with the longitudinal direction A aligning with the waistline direction X of the waistline portion 31. The joining regions 39 each include at least partially a non-formation region where the intersection 4a of the first bonding section 4 and the elastic member 10 is not formed.

This configuration causes each joining region 39 joining the front abdomen portion 32 to the rear back portion 33 to include at least partially the non-formation region where the intersection 4a of the first bonding section 4 and the elastic member 10 is not formed, so that the elastic member 10 is not bonded to the sheets 2a, 2b. Thus, each joining region 39 does not expand and contract with the elastic member 10, so that flexibility of the sheets 2a, 2b can be maintained.

The disposable diaper 30, which is a wearing article of the present embodiment, includes the joining regions 39 extending linearly in the width direction B, and at least one second bonding section 42 that linearly extends in the width direction B and that is formed between each of the joining regions 39 and the first bonding section 4 closest to the corresponding one of the joining regions 39. This configuration enables the second bonding section 42 extending linearly to bond an end portion of the elastic member 10 to the sheets 2a, 2b with a good appearance at a position closer to the joining region 39 than the first bonding section 4. As a result, the design properties in the disposable diaper 30 (wearing article), particularly, in a portion near the joining region 39, is further improved.

(7)

The disposable diaper 30, which is a wearing article of the present embodiment, includes a plurality of second bonding sections 42 formed side by side. This configuration enables the plurality of second bonding sections 42 to reliably hold the end portion of the elastic member 10.

(8)

The disposable diaper 30, which is a wearing article of the present embodiment, includes the absorbent body 37 that absorbs liquid. The absorbent body 37 is overlapped with and fixed to the composite stretchable member 1 constituting the waistline portion 31. In a region other than the overlapped portion S where the absorbent body 37 is overlapped with the composite stretchable member 1, the intersection 4a of the first handing section 4 and the elastic member 10 are formed, and the elastic member 10 is disconnected in the overlapped portion S.

This configuration causes no intersection 4a of the first bonding section 4 and the elastic member 10 to be formed in the overlapped portion S where the absorbent body 37 is overlapped with the composite stretchable member 1 constituting the waistline portion 31, and causes the elastic member 10 to be disconnected. Thus, the overlapped portion S does not partially contract, so that the absorbent body 37 can be stably held in the waistline portion 31, thereby enabling occurrence of wrinkles in the absorbent body 37 to be reduced.

(9)

The disposable diaper 30, which is a wearing article of the present embodiment, includes the overlapped portion S (in the present embodiment, the weakened region 32*b* including the overlapped portion S) having an edge extending linearly in the width direction Y, and at least one third bonding section 43 that extends linearly in the width direction B and that is formed between the overlapped portion S and the first bonding section 4 closest to the overlapped portion S.

This configuration enables the third bonding section 43 extending linearly to bond the end portion of the elastic member 10 to the sheets 2*a*, 2*b* with a good appearance at a position closer to the overlapped portion S than the first bonding section 4, and thus the design properties in the disposable diaper 30 (wearing article), particularly, in a portion near the overlapped portion 5, is further improved. Although at least one third bonding section 43 needs to be provided, a plurality of third bonding sections 43 may be provided.

Other Embodiments

Although in the above embodiment, the disposable diaper of an underpants-type has been described as an example of the wearing article, the present invention is not limited thereto, and thus can be applied to any wearing articles of various forms including the composite stretchable member and the absorbent body 37. Thus, the wearing article of the present invention can be applied to not only disposable diapers of an underpants-type but also disposable diapers of various forms such as a tape type and a pad type, and also can be applied to sanitary napkins and the like.

Summary of Embodiment

The above embodiment is summarized as follows.

The composite stretchable member according to the present invention is stretchable in a specific direction and includes two sheets facing each other, and a plurality of elastic members extending along the specific direction and being stretchable in the specific direction between the sheets, the sheets being bonded to each other at a plurality of first bonding sections, each of the first bonding sections continuously extending along an intersecting direction intersecting the specific direction to intersect the plurality of elastic members, each of the elastic members being bonded to each of the sheets at an intersection with the corresponding one of the first bonding sections, each of the first bonding sections having a wavy line shape extending in the intersecting direction with convex portions and concave portions that alternately appear continuously, and being disposed in a state where the convex portions and the concave portions are overlapped each other when viewed from the specific direction in at least a part of two adjacent first bonding sections.

This configuration causes pleats in a wavy line shape to be formed along the respective first bonding sections in a wavy line shape when the composite stretchable member contracts, and thus enables a unique texture to be expressed by the composite stretchable member. As a result, a wearing article having high design properties can be manufactured using the composite stretchable member.

The composite stretchable member above preferably includes the two adjacent first bonding sections that are disposed with both the bonding sections coinciding in phase with each other in the intersecting direction in at least one region.

This configuration enables forming a plurality of pleats in a wavy line shape coinciding in phase when the composite stretchable member contracts, and thus enables manufacturing a wearing article having higher design properties.

The composite stretchable member above preferably includes the plurality of first bonding sections disposed at intervals that are set to have a space between the two adjacent first bonding sections, being closed by the convex portion of at least one of the two first bonding sections when viewed from the intersecting direction.

This configuration causes the convex portion of any one of the two first bonding sections to exist between the two adjacent first bonding sections when viewed from the intersecting direction, so that fluctuations in pressure under which the two sheets are sandwiched to form the plurality of first bonding sections can be reduced at any position in the intersecting direction, and thus the first bonding sections without unevenness can be formed. This configuration also enables reducing vibrations of means for applying pressure to the two sheets to form the first bonding sections.

A wearing article of the present invention includes a waistline portion disposed around a waistline of a wearer, wherein at least a part of the waistline portion is formed of the composite stretchable member. This configuration enables manufacturing a wearing article having high design properties.

The wearing article described above is preferably configured as follows: the waistline portion has a front abdomen portion disposed on the front of the abdomen of a wearer and a rear back portion disposed on the buttocks of the wearer; the waistline portion is formed in an annular shape by joining the front abdomen portion to the rear back portion with a pair of joining regions; the front abdomen portion and the rear back portion are formed of the composite stretchable member; the composite stretchable member is disposed with the specific direction aligning with a waistline direction of the waistline portion; and the regions each include at least partially a non-formation region where an intersection of the first bonding section and the elastic member is not formed.

This configuration causes each joining region joining the front abdomen portion to the rear back portion to include at least partially the non-formation region where the intersection of the first bonding section and the elastic member is not formed, so that the elastic member is not bonded to the sheets. Thus, each joining region does not expand and contract with the elastic member, so that flexibility of the sheets can be maintained.

The wearing article described above preferably includes the joining regions extending linearly in the intersecting direction, and at least one second bonding section that linearly extends in the intersecting direction and that is formed between each of the joining regions and the first bonding section closest to the corresponding one of the joining regions.

This configuration enables the second bonding section extending linearly to bond an end portion of the elastic member to the sheets with a good appearance at a position closer to the joining region than the first bonding section, and thus the design properties in the wearing article is further improved.

The wearing article above preferably includes a plurality of second bonding sections formed side by side.

This configuration enables the plurality of second bonding sections to reliably hold the end portion of the elastic member.

The wearing article described above preferably further includes an absorbent body that absorbs liquid, wherein the absorbent body is overlapped with and fixed to the composite elastic member constituting the waistline portion, in a region other than an overlapped portion in the composite stretchable member where the absorbent body is overlapped with the composite stretchable member, an intersection of the first bonding section and the elastic member are formed, and the elastic member is disconnected in the overlapped portion.

This configuration causes no intersection of the first bonding section and the elastic member to be formed in the overlapped portion where the absorbent body is overlapped with the composite stretchable member constituting the waistline portion, and causes the elastic member to be disconnected. Thus, the overlapped portion does not partially contract, so that the absorbent body can be stably held in the waistline portion, thereby enabling occurrence of wrinkles in the absorbent body to be reduced.

The wearing article described above preferably includes the overlapped portion having an edge extending linearly in the intersecting direction, and at least one third bonding section that extends linearly in the intersecting direction and that is formed between the overlapped portion and the first bonding section closest to the overlapped portion.

This configuration enables the third bonding section extending linearly to bond an end portion of the elastic member to the sheets with a good appearance at a position closer to the overlapped portion than the first bonding section, and thus the design properties in the wearing article is further improved.

As described above, the composite stretchable member of the present embodiment and the wearing article using the same enable improvement in design properties of the composite stretchable member and the wearing article using the same by forming a plurality of pleats in a wavy line shape when the composite stretchable member contracts.

The invention claimed is:

1. A composite stretchable member that is stretchable in a longitudinal direction and includes a part to be used as a waistline portion of each of a plurality of wearing articles, the composite stretchable member comprising:

two sheets facing each other; and a plurality of elastic members extending along the longitudinal direction and being stretchable in the longitudinal direction between the sheets, the sheets being bonded to each other at a plurality of first bonding sections, each of the first bonding sections continuously extending along a width direction intersecting the longitudinal direction to intersect the plurality of elastic members, each of the elastic members being bonded to each of the sheets at an intersection with the corresponding one of the first bonding sections, and each of the first bonding sections having a wavy line shape extending in the width direction with convex portions and concave portions that alternately appear continuously, and being disposed in a state where the convex portions and the concave portions are overlapped each other when viewed from the longitudinal direction in at least a part of two adjacent first bonding sections, wherein the part includes:

a pair of joining regions provided at the opposite ends of the part, and extending linearly in the width direction, and a second bonding section formed between one of the pair of joining regions and the first bonding section closest to the one joining region and another second bonding section formed between the other joining region and the first bonding section closest to the other joining region, the second bonding sections linearly extending an entire length of the width direction.

2. The composite stretchable member according to claim 1, wherein
the two adjacent first bonding sections are disposed with both the bonding sections coinciding in phase with each other in the width direction in at least one region.

3. The composite stretchable member according to claim 1, wherein
the plurality of first bonding sections is disposed at intervals that are set to have a space between the two adjacent first bonding sections, being closed by the convex portion of at least one of the two first bonding sections when viewed from the width direction.

4. A wearing article comprising a waistline portion disposed around a waistline of a wearer, wherein at least a part of the waistline portion is formed of the composite stretchable member according to claim 1.

5. The wearing article according to claim 4, wherein
the waistline portion has a front abdomen portion disposed on a front of an abdomen of a wearer and a rear back portion disposed on buttocks of the wearer,
the waistline portion is formed in an annular shape by joining the front abdomen portion to the rear back portion with a pair of the joining regions,
the front abdomen portion and the rear back portion are formed of the composite stretchable member,
the composite stretchable member is disposed with the longitudinal direction aligning with a waistline direction of the waistline portion, and
the joining regions each include at least partially a non-formation region where an intersection of the first bonding section and the elastic member is not formed.

6. The wearing article according to claim 5, wherein a plurality of the second bonding sections is formed side by side.

7. The wearing article according to claim 4, further comprising:
an absorbent body that absorbs liquid,
wherein the absorbent body is overlapped with and fixed to the composite stretchable member constituting the waistline portion, and
in a region other than an overlapped portion in the composite stretchable member where the absorbent body is overlapped with the composite stretchable member, an intersection of the first bonding section and the elastic member are formed, and the elastic member is disconnected in the overlapped portion.

8. The wearing article according to claim 7, wherein
the overlapped portion has an edge extending linearly in the width direction, and
at least one third bonding section extending linearly in the width direction is formed between the overlapped portion and the first bonding section closest to the overlapped portion.

9. The composite stretchable member according to claim 2, wherein
the plurality of first bonding sections is disposed at intervals that are set to have a space between the two adjacent first bonding sections, being closed by the convex portion of at least one of the two first bonding sections when viewed from the width direction.

10. The wearing article according to claim 5, further comprising:
an absorbent body that absorbs liquid, wherein the absorbent body is overlapped with and fixed to the composite stretchable member constituting the waistline portion, and in a region other than an overlapped portion in the composite stretchable member where the absorbent body is overlapped with the composite stretchable member, an intersection of the first bonding section and the elastic member are formed, and the elastic member is disconnected in the overlapped portion.

11. The wearing article according to claim 6, further comprising:

an absorbent body that absorbs liquid, wherein the absorbent body is overlapped with and fixed to the composite stretchable member constituting the waistline portion, and in a region other than an overlapped portion in the composite stretchable member where the absorbent body is overlapped with the composite stretchable member, an intersection of the first bonding section and the elastic member are formed, and the elastic member is disconnected in the overlapped portion.

12. The wearing article according to claim 10, wherein the overlapped portion has an edge extending linearly in the width direction, and at least one third bonding section extending linearly in the width direction is formed between the overlapped portion and the first bonding section closest to the overlapped portion.

13. The wearing article according to claim 11, wherein the overlapped portion has an edge extending linearly in the width direction, and at least one third bonding section extending linearly in the width direction is formed between the overlapped portion and the first bonding section closest to the overlapped portion.

* * * * *